(12) United States Patent
Tani et al.

(10) Patent No.: US 7,199,260 B2
(45) Date of Patent: Apr. 3, 2007

(54) PROCESS FOR REDUCTIVE DEHALOGENATION

(75) Inventors: Yuichiro Tani, Tokyo (JP); Keiji Nakayama, Tokyo (JP); Kenji Sakuratani, Tokyo (JP); Koji Sato, Tokyo (JP)

(73) Assignee: Daiichi Pharmaceutical Co., Ltd., Tokyo (JP)

( * ) Notice: Subject to any disclaimer, the term of this patent is extended or adjusted under 35 U.S.C. 154(b) by 0 days.

(21) Appl. No.: 10/541,204

(22) PCT Filed: Jan. 7, 2004

(86) PCT No.: PCT/JP2004/000018

§ 371 (c)(1),
(2), (4) Date: Jul. 5, 2005

(87) PCT Pub. No.: WO2004/060851

PCT Pub. Date: Jul. 22, 2004

(65) Prior Publication Data

US 2006/0052626 A1    Mar. 9, 2006

(30) Foreign Application Priority Data

Jan. 7, 2003  (JP) ............................. 2003-001300

(51) Int. Cl.
*C07C 69/74*  (2006.01)
(52) U.S. Cl. ..................................... 560/124
(58) Field of Classification Search ................ 560/124, 560/125; 570/123, 124, 133, 176
See application file for complete search history.

(56) References Cited

FOREIGN PATENT DOCUMENTS

| | | |
|---|---|---|
| GB | 1 594 224 | 7/1981 |
| JP | 06-157418 | 6/1994 |
| JP | 06157418 | * 6/1994 |
| WO | 95/04712 | 2/1995 |

OTHER PUBLICATIONS

Rolla et al., Sodium Borohydride Reactions under Phase-Transfer Conditions: Conversion of Halides and Sulphonate Esters to Alkanes; J. Org. Chem., 1981, 46. 3909-3911.*
Kirk-Othmer Encyclopedia of Chemical Technology Copyright © 1993 by John Wiley & Sons, Inc. pp. 1-10.*
Franco Rolla, J. Org. Chem 1981, 46, 3909-3911 Sodium Borohydride Reductions under Phase-Transfer Conditions: Conversation of Halides and Sulfonate Esters to Alkanes.

* cited by examiner

*Primary Examiner*—Thurman Page
*Assistant Examiner*—Karl Puttlitz
(74) *Attorney, Agent, or Firm*—Oblon, Spivak, McClelland, Maier & Neustadt, P.C.

(57) ABSTRACT

A method of producing 2-fluorocyclopropane-1-carboxylic acid ester, which comprise by allowing a compound represented by the following formula (1):

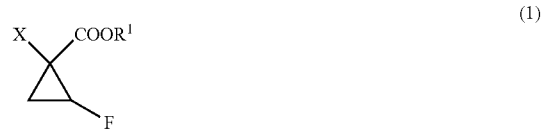

(1)

wherein X represents a chlorine atom, a bromine atom or an iodine atom; and $R^1$ represents an alkyl group having 1 to 8 carbon atoms, an aryl group having 6 to 12 carbon atoms, an alkenyl group having 2 to 8 carbon atoms, or an aralkyl group composed of an aryl group having 6 to 12 carbon atoms and an alkylene group having 1 to 6 carbon atoms; to react with a reducing agent in the presence of a phase transfer catalyst.

According to the production method of the present invention, the reaction time of dehalogenation can be greatly shortened.

20 Claims, No Drawings

PROCESS FOR REDUCTIVE DEHALOGENATION

TECHNICAL FIELD

The present invention relates to a method of producing fluorocyclopropane useful for producing an excellent compound for pharmaceutical agents or agricultural chemicals.

BACKGROUND ART

Within the synthetic new quinolone antibacterial agents, quinolone derivatives containing a 1,2-cis-2-fluorocyclopropyl group as a substituent at the 1-position have a strong antibacterial activity and are highly safe at the same time, and thus expected to be an excellent synthetic antibacterial agent. To prepare such 1,2-cis-2-fluorocyclopropyl group, 1,2-cis-2-fluorocyclopropane-1-carboxylic acid is useful. This compound is produced by dechlorinating 1-chloro-2-fluorocyclopropane-1-carboxylic acid ester in dimethyl sulfoxide in the presence of sodium borohydride (Japanese Patent Application Laid-Open No. 6-157418). However, this dechlorination reaction has a problem that when a stirring blade is used in the stirring step with the view of industrial production, it takes several days to complete the reaction, and therefore establishment of a convenient production method with a reduced reaction time has been desired. In addition, since dimethyl sulfoxide generates dimethyl sulfide which is responsible for foul odor during the reaction, there has been a problem of harmful effects on the environment.

Under such circumstances, an object of the present invention is to provide a method of producing 2-fluorocyclopropane-1-carboxylic acid ester by efficiently dehalogenating 1-halogeno-2-fluorocyclopropane-1-carboxylic acid ester, which method is also applicable to apparatuses for industrial production.

DISCLOSURE OF THE INVENTION

The inventors of the present invention have conducted intensive studies on dehalogenation reaction of 1-halogeno-2-fluorocyclopropane-1-carboxylic acid ester, and found a method of producing 2-fluorocyclopropane-1-carboxylic acid ester which comprises allowing 1-halogeno-2-fluorocyclopropane-1-carboxylic acid ester to react with a reducing agent in a two-phase system in the presence of a phase transfer catalyst, which method is also applicable to industrial scale production, and has completed the present invention.

Accordingly, the present invention provides a method of producing 2-fluorocyclopropane-1-carboxylic acid ester (2), characterized by allowing a compound represented by the following formula (1):

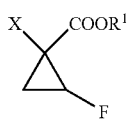

(1)

wherein X represents a chlorine atom, a bromine atom or an iodine atom; and $R^1$ represents an alkyl group having 1 to 8 carbon atoms, an aryl group having 6 to 12 carbon atoms, an alkenyl group having 2 to 8 carbon atoms, or an aralkyl group composed of an aryl group having 6 to 12 carbon atoms and an alkylene group having 1 to 6 carbon atoms; to react with a reducing agent in the presence of a phase transfer catalyst. The use of the phase transfer catalyst enables an efficient two-phase reaction to proceed between an organic phase containing 1-halogeno-2-fluorocyclopropane-1-carboxylic acid ester and an aqueous phase containing a reducing agent.

BEST MODE FOR CARRYING OUT THE INVENTION

In the formula (1), X represents a chlorine atom, a bromine atom or an iodine atom, with a chlorine atom being preferred.

$R^1$ represents an alkyl group having 1 to 8 carbon atoms, an aryl group having 6 to 12 carbon atoms, an alkenyl group having 2 to 8 carbon atoms, or an aralkyl group composed of an aryl group having 6 to 12 carbon atoms and an alkylene group having 1 to 6 carbon atoms. Examples of the alkyl group having 1 to 8 carbon atoms include a methyl group, an ethyl group, a propyl group, an isopropyl group, a butyl group, a sec-butyl group, a t-butyl group, a pentyl group, a cyclopropyl group, a cyclobutyl group and a cyclopentyl group. Examples of the aryl group having 6 to 12 carbon atoms include a phenyl group and a naphthyl group. The aryl group may be further substituted by an alkyl group having 1 to 6 carbon atoms such as a methyl group, an ethyl group, a propyl group, an isopropyl group, a butyl group, a sec-butyl group or a t-butyl group, an alkoxy group having 1 to 6 carbon atoms such as a methoxy group, an ethoxy group or a propoxy group, a cyano group, a nitro group, a halogen atom, an amino group, a hydroxy group, a carboxy group or the like. Examples of the alkenyl group having 2 to 8 carbon atoms include a vinyl group and a 1-isopropenyl group. Examples of the aralkyl group composed of anaryl group having 6 to 12 carbon atoms and an alkylene group having 1 to 6 carbon atoms include a benzyl group and a phenethyl group. The aryl group constituting the aralkyl group may be further substituted by the above-mentioned alkyl group having 1 to 6 carbon atoms, the above-mentioned alkoxy group having 1 to 6 carbon atoms, a cyano group, a nitro group, a halogen atom, an amino group, a hydroxy group, a carboxy group or the like.

As $R^1$, an alkyl group having 1 to 8 carbon atoms is preferable, and a methyl group, an ethyl group, a butyl group, a sec-butyl group and a t-butyl group are more preferable, and a t-butyl group is even more preferable. When $R^1$ is a t-butyl group, an effect of preventing generation of a by-product (1-chloro-2-fluoro-1-hydroxymethyl cyclopropane) can be observed.

The compound (1) can be easily synthesized from 1-chloro-cyclopropane-1,2-dicarboxylic acid-1-t-butyl ester according to a method described, for example, in Japanese Patent Application Laid-Open No. 5-301827.

As a reducing agent used in the producing method of the present invention, a compound represented by the following formula (3)

$$MBH_m R^2_n \qquad (3)$$

can be used, wherein M represents an alkali metal atom such as lithium, sodium or potassium, and $R^2$ represents a hydrogen atom, a cyano group, an alkoxy group or an acyloxy group. As the alkoxy group, the aforementioned alkoxy groups having 1 to 6 carbon atoms are preferable. Examples of the acyloxy group include an alkylcarbonyloxy group, an arylcarbonyloxy group and an aralkylcarbonyloxy group. These alkoxy groups or acyloxy groups may be further substituted by a halogen atom or the like. Specific examples of the alkoxy group or the acyloxy group include an acetyloxy group, a trifluoroacetyloxy group, a benzoyloxy group and a benzylcarbonyloxy group. It may also be an N-isobutyloxycarbonylprolyloxy group or an N-benzyloxycarbonylprolyloxy group. Here, m is an integer of 1 to 4 and n is an integer of 0 to 3, and the sum of m and n is 4.

The compound (3) may be generally selected from sodium borohydride, lithium borohydride, zinc borohydride, sodium cyano borohydride and sodium alkoxyborohydride. As an alkoxy group of sodium alkoxyborohydride, alkoxy groups having 1 to 6 carbon atoms are preferable, and sodium borohydride is more preferable.

The reducing agent is used in an amount in the range of preferably from 1.0 to 10.0 equivalents, more preferably 1.5 to 3.5 equivalents with regard to the compound represented by the formula (1).

Examples of the phase transfer catalyst used herein include quaternary ammonium salts such as tetraethylammonium chloride, tetrabutylammonium chloride, tetrabutylammonium bromide, tetrabutylammonium iodide, tetrabutylammonium hydrogen sulfate and trioctylmethylammonium chloride, quaternary phosphonium salts such as tetrabutylphosphonium chloride and tetrabutylphosphonium bromide, and crown ether. Among these, quaternary ammonium salts are preferable, and as the quaternary ammonium salt, trioctylmethylammonium chloride, tetrabutylammonium chloride, tetrabutylammonium bromide and tetrabutylammonium hydrogen sulfate are preferable, with trioctylmethylammonium chloride being more preferable. When using a quaternary phosphonium salt, tetrabutylphosphonium chloride is preferable.

The phase transfer catalyst is used in the range of preferably from 1.0 to 30% by mole, more preferably from 10 to 20% by mole with regard to the compound represented by the formula (1).

Referring to the reaction solvent, it is preferable to use a combination of water and any of the solvents listed below. As the solvent, ether solvents such as dialkyl ether (diethyl ether, diisopropyl ether, methyl t-butyl ether, ethyl t-butyl ether, methyl n-butyl ether, ethyl n-butyl ether, cyclopentyl methyl ether and the like); aromatic solvents such as toluene and benzene; ester solvents such as ethyl acetate; polar solvents such as tetrahydrofuran, acetonitrile, N,N-dimethylformamide, dimethyl sulfoxide and alcohol; aliphatic solvents such as hexane, heptane, octane and cyclohexane; and the like may be used. Of these non-polar solvents are preferable, and diisopropyl ether, methyl t-butyl ether, cyclopentyl methyl ether, toluene, hexane, heptane, octane and cyclohexane are more preferable, and methyl t-butyl ether and heptane are particularly preferable. In addition, a mixture of two or more solvents may be used. In view of the reaction rate, the solubility and the proportion of generated diastereomers of the compound (2), methyl t-butyl ether and heptane are preferable. The mixing ratio of water and the solvent is in the range of preferably from 1:8 to 1:1, more preferably from 1:4 to 1:1. The total amount of solvent is in the range of preferably from 1 to 5 (v/w), more preferably from 2 to 4 (v/w) based on the compound represented by the formula (1).

As the reaction solvent, water alone may be used, or a diluted hydrochloric acid or an aqueous sodium hydroxide solution may also be used.

In the method of production according to the present invention, the compound (2) maybe produced by a reaction with a reducing agent in the presence of a phase transfer catalyst for 1 to 24 hours. Depending on the kind of the solvent, the reaction may be completed in a few hours.

The reaction may be effected in a temperature range of from 5 to 60° C., preferably from 10 to 50° C., more preferably from 15 to 30° C. When the calorific value is great upon the reaction, it is desirable to effect the reaction under cooling.

After completion of the reaction, the compound (2) is collected from the reaction mixture according to a method usually employed. For example, the compound (2) can be collected by removing inorganic substances as an aqueous layer and distilling off the solvent in the organic layer. The obtained target compound can be further purified by distillation or chromatography according to need. The compound (2) can be prepared by these procedures.

The configuration of the fluorine atom at the 2-position and the carboxylic acid moiety at the 1-position of the compound (2) includes two types: one is a configuration in which both are present on the same side of a plane of a cyclopropane ring (cis-form) and the other is a configuration in which each is present on a different side of a plane of a cyclopropane ring (trans-form). According to the method of production of the present invention, the cis-form and the trans-form are produced in a proportion range of 87:13 to 97:3. The method of production of the present invention is thus excellent for producing 1,2-cis-2-fluorocyclopropane-1-carboxylic acid which is a synthetic intermediate for synthetic new quinolone antibacterial agents. In the method of production of the present invention, the content of the trans-form is decreased compared to the content thereof before the start of the reaction, while the content of the cis-form in the reaction mixture is increased after the reaction. Accordingly, the objective cis-forms can be advantageously obtained by the method of the present invention.

1,2-cis-2-Fluorocyclopropane-1-carboxylic acid can be produced by optical resolution according to a usual method after deriving 2-fluorocyclopropane-1-carboxylic acid from 2-fluorocyclopropane-1-carboxylic acid ester which is a mixture of diastereomers obtained by the method of production according to the present invention.

Optical resolution can be carried out by preferential crystallization, diastereomer synthesis, an enzymatic method, chromatography or others. Specifically, for example, after hydrolyzing 2-fluorocyclopropane-1-carboxylic acid ester, the hydrolyzed product (racemic form) is allowed to react with an optical resolution agent to prepare a mixture of diastereomer salts of optically active 2-fluorocyclopropane-1-carboxylic acid and an optical resolution agent, and after separating desired diastereomer salts by precipitation or the like, the separated diastereomer salts are treated with alkali. Then the obtained optically active compound is isolated.

In this regard, since cis-form and trans-form of an ester compound can be separated by a distillation procedure, efficiency of optical resolution can be increased by preparing an ester compound from which trans-forms are removed by a distillation procedure in advance and using a carboxylic acid compound obtained by hydrolyzing the ester compound.

As the optical resolution agent, (+) and (−)-N-benzyl-α-methylbenzylamine, (+) and (−)-α-methylbenzylamine, (+) and (−)-α-ethylbenzylamine, (+) and (−)-(p-tolyl)ethylamine, (+) and (−)-phenyl-2-(p-tolyl)ethylamine, (+) and (−)-erythro-2-amino-1,2-diphenylethanol, (+) and (−)-1-(1-naphthyl)ethyl amine, (+) and (−)-cis-2-(benzylamino)cyclohexane methanol, (+) and (−)-α-methyl-p-nitrobenzy-

EXAMPLES

The present invention is described by means of Examples, which is not constructed as limiting the present invention.

Example 1

Production of t-butyl 2-fluorocyclopropane-1-carboxylate (2a) 1

To a solution heated to 40° C. obtained by dissolving t-butyl 1-chloro-2-fluorocyclopropane-1-carboxylate (tertiary butyl ester; cis/trans=62/38; in this specification, regardless of the presence or absence of a halogen atom at the 1-position, a compound in which a fluorine atom and a carboxylic acid ester moiety are present on the same side of a plane of a cyclopropane ring is referred to as cis-form; 0.97 g, 5.0 mmoles) and tetrabutylammonium bromide (161 mg, 10% by mole) in methyl t-butyl ether (1.94 mL), an aqueous solution of sodium borohydride (concentration: 1 g/2.6 mL, 1.45 mL) was gradually added with stirring using a stirring blade. After the addition, the mixture was stirred using a stirring blade at 40° C. for 20 hours, and then water was added to the reaction mixture. Diisopropyl ether was added to the mixture to conduct extraction (30 mL×3) to give a diisopropyl ether solution containing 424 mg of the title compound (2a) (quantitation by high performance liquid chromatography, yield 53%). HPLC analysis conditions: column: MERCK Chromorith Performance RP-18 100-4.6 mm, mobile phase: pH 4.2 phosphate buffer/acetonitrile=70/30, flow rate: 1.0 mL/min, detection wavelength: 220 nm. Further, gas chromatography analysis was conducted and cis/trans=95/5 was found [analysis conditions: detector: FID, column: GLscience, NEUTRA BOND-5, 30 m×0.25 mm, temperature of vaporization chamber: 250° C., detector temperature: 250° C, carrier gas: nitrogen (80 kPa), hydrogen (60 kPa), air (50 kPa)].

Example 2

Production of t-butyl 2-fluorocyclopropane-1-carboxylate (2a) 2

The same procedures as in Example 1 were conducted except that hexane was used as a reaction solvent instead of methyl t-butyl ether, and the mixture was stirred at 40° C. for 6 hours. Subsequently, the same treatment as in Example 1 was conducted, and a diisopropyl ether solution containing a compound (2a) was analyzed by HPLC and a yield of 59% was found. GC analysis was conducted and cis/trans=96/4 was found.

Example 3

Production of t-butyl 2-fluorocyclopropane-1-carboxylate (2a) 3 t-Butyl 1-chloro-2-fluorocyclopropane-1-carboxylate (cis/trans=62/38, 3 g, 15.4 mmoles) and trioctylmethylammonium chloride (1.25 g, 20% by mole) were dissolved in heptane (6 mL), and sodium borohydride (1.75 g, 46.2 mmoles) was added to the solution at room temperature. After the addition, water (4.5 mL) was added to the solution and the mixture was stirred for 3 hours at the same temperature. After adding water to the reaction solution, methyl t-butyl ether was added to conduct extraction (50 mL×3) to give a methyl t-butyl ether solution containing 2.22 g of the title compound (2a) (quantitation by high performance liquid chromatography, yield 89%). GC analysis was conducted and cis/trans=90/10 was found.

Example 4

Production of t-butyl 2-fluorocyclopropane-1-carboxylate (2a) 4 t-Butyl 1-chloro-2-fluorocyclopropane-1-carboxylate (cis/trans=62/38, 1 g, 5.1 mmoles) and trioctylmethylammonium chloride (415.3 mg, 20% by mole) were dissolved in heptane (2 mL), and sodium borohydride (583.1 mg, 15.4 mmoles) was added to the solution at 40° C. After the addition, a 0.1 N aqueous sodium hydroxide solution (1.5 mL) was added to the solution and the mixture was stirred for 7 hours at the same temperature. After adding water to the reaction mixture, methyl t-butyl ether was added to conduct extraction (30 mL×3) to give a methyl t-butyl ether solution containing 663.7 mg of the title compound (2a) (quantitation by high performance liquid chromatography, yield 77%). GC analysis was conducted and cis/trans=91/9 was found.

Example 5

Production of t-butyl 2-fluorocyclopropane-1-carboxylate (2a) 5

In the same manner as in Example 4 except that the mixture was stirred for 24 hours after adding a 0.1 N aqueous sodium hydroxide solution (1.5 mL), a methyl t-butyl ether solution containing 543.2 mg of the title compound (2a) was obtained (quantitation by high performance liquid chromatography, yield 66%). GC analysis was conducted and cis/trans=88/12 was found.

Example 6

Production of t-butyl 2-fluorocyclopropane-1-carboxylate (2a) 6 t-Butyl 1-chloro-2-fluorocyclopropane-1-carboxylate (cis/trans=62/38, 1 g, 5.1 mmoles) and trioctylmethylammonium chloride (415.3 mg, 20% by mole) were dissolved in toluene (2 mL), and sodium borohydride (583.1 mg, 15.4 mmoles) was added to the solution at 40° C. After the addition, water (1.5 mL) was added to the solution and the mixture was stirred for 24 hours at the same temperature. After adding water to the reaction mixture, methyl t-butyl ether was added to conduct extraction (30 mL×3) to give a methyl t-butyl ether solution containing 477.4 mg of the title

--- lamine and the like may be used and appropriately selected depending on the optical isomer of 2-fluorocyclopropane-1-carboxylic acid to be obtained.

The optical resolution agent is preferably reacted in dialkyl ether, and examples of dialkyl ether include methyl t-butyl ether, ethyl t-butyl ether, methyl n-butyl ether, ethyl n-butyl ether and cyclopentyl methyl ether. Of these, methyl t-butyl ether is preferably used.

For alkali treatment of diastereomer salt, bases like alkali metal hydroxides such as sodium hydroxide and potassium hydroxide, alkali metal carbonates such as sodium carbonate and potassium carbonate and alkali metal hydrogen carbonates such as sodium hydrogen carbonate and potassium hydrogen carbonate are usually used.

compound (2a) (quantitation by high performance liquid chromatography, yield 58%). GC analysis was conducted and cis/trans=89/11 was found.

Example 7

Production of t-butyl 2-fluorocyclopropane-1-carboxylate (2a) 7 t-Butyl 1-chloro-2-fluorocyclopropane-1-carboxylate (cis/trans=62/38, 1 g, 5.1 mmoles) and trioctylmethylammonium chloride (415.3 mg, 20% by mole) were dissolved in cyclopentyl methyl ether (2 mL), and sodium borohydride. (583.1 mg, 15.4 mmoles) was added to the solution at 40° C. After the addition, water (1.5 mL) was added to the solution and the mixture was stirred for 24 hours at the same temperature. After adding water to the reaction mixture, methyl t-butyl ether was added to conduct extraction (30 mL×3) to give a methyl t-butyl ether solution containing 535.0 mg of the title compound (2a) (quantitation by high performance liquid chromatography, yield 65%). GC analysis was conducted and cis/trans=89/11 was found.

Example 8

Production of t-butyl 2-fluorocyclopropane-1-carboxylate (2a) 8

In the same manner as in Example 7 except that the solvent was changed to octane, a methyl t-butyl ether solution containing 609.1 mg of the title compound (2a) was obtained (quantitation by high performance liquid chromatography, yield 74%). GC analysis was conducted and cis/trans=89/11 was found.

Example 9

Production of t-butyl 2-fluorocyclopropane-1-carboxylate (2a) 9

In the same manner as in Example 7 except that the solvent was changed to hexane, a methyl t-butyl ether solution containing 592.6 mg of the title compound (2a) was obtained (quantitation by high performance liquid chromatography, yield 72%). GC analysis was conducted and cis/trans=90/10 was found.

Example 10

Production of t-butyl 2-fluorocyclopropane-1-carboxylate (2a) 10 t-Butyl 1-chloro-2-fluorocyclopropane-1-carboxylate (cis/trans=62/38, 1 g, 5.1 mmoles) and tetrabutylammonium chloride (285.6 mg, 20% by mole) were dissolved in methyl t-butyl ether (3 mL), and sodium borohydride (583.1 mg, 15.4 mmoles) was added to the solution at 40° C. After the addition, 0.02 N hydrochloric acid (1.5 mL) was added to the solution and the mixture was stirred for 22 hours at the same temperature. After adding water to the reaction mixture, methyl t-butyl ether was added to conduct extraction (30 mL×3) to give a methyl t-butyl ether solution containing 395.0 mg of the title compound (2a) (quantitation by high performance liquid chromatography, yield 48%). GC analysis was conducted and cis/trans=92/8 was found.

Example 11

Production of t-butyl 2-fluorocyclopropane-1-carboxylate (2a) 11 t-Butyl 1-chloro-2-fluorocyclopropane-1-carboxylate (cis/trans=62/38, 1 g, 5.1 mmoles) and tetrabutylammonium hydrogen sulfate (349.0 mg, 20% by mole) were dissolved in methyl t-butyl ether (3 mL), and sodium borohydride (583.1 mg, 15.4 mmoles) was added to the solution at 40° C. After the addition, 0.02 N hydrochloric acid (1.5 mL) was added to the solution and the mixture was stirred for 24 hours at the same temperature. After adding water to the reaction mixture, methyl t-butyl ether was added to conduct extraction (30 mL×3) to give a methyl t-butyl ether solution containing 395.0 mg of the title compound (2a) (quantitation by high performance liquid chromatography, yield 58%). GC analysis was conducted and cis/trans=93/7 was found.

Reference Example 1

Production of (1S, 2S)-2-fluorocyclopropane-1-carboxylic acid

A 5 N aqueous sodium hydroxide solution (6.8 mL) was added to an ethanol solution (6.8 mL) of compound (2a) obtained in the Examples to conduct a reaction at 50° C. for 12 hours. After the completion of the reaction, the mixture was cooled to room temperature and ethanol was removed under reduced pressure. To the obtained residue was added 1 N hydrochloric acid under cooling with ice so that the pH became pH 2 or lower, and extraction by methyl t-butyl ether was conducted (15 mL×2). The organic layer was dried over magnesium sulfate and methyl t-butyl ether was removed under reduced pressure to give a racemic form of 2-fluorocyclopropane-1-carboxylic acid. The racemic form was dissolved in methyl t-butyl ether (30 mL) and with stirring the mixture at room temperature, (R)-(+)-N-benzyl-α-methyl-benzylamine (1.0 equivalent) was added thereto dropwise. The precipitated diastereomer salt of 1,2-cis-2-fluorocyclopropane-1-carboxylic acid and (R)-(+)-N-benzyl-α-methyl-benzylamine was recrystallized in isopropyl ether (45 mL) (yield: 1.51 g, optical purity: 99% e.e.). Subsequently, a 2 N aqueous sodium hydroxide solution (4.7 mL) was added to the obtained diastereomer salt, and the mixture was washed with chloroform (10 mL×2), and the aqueous layer was neutralized with 6 N hydrochloric acid (5mL). After the neutralization, extraction by ethyl acetate was conducted (10 mL×3), and the organic layer was dried over magnesium sulfate and ethyl acetate was removed under reduced pressure to give the title compound (yield: 478.3 mg, optical purity: 99% e.e.).

INDUSTRIAL APPLICABILITY

By using the method of production of the present invention, the reaction time of a dehalogenation reaction of 1-halogeno-2-fluorocyclopropane-1-carboxylic acid ester can be significantly shortened as compared to the reaction time in previous methods. In particular, even in the case of using an apparatus for industrial production, the reaction can be completed in a shorter time. Furthermore, because dimethyl sulfoxide is not used as a reaction solvent in the method of production according to the present invention, the problem of generation of dimethyl sulfide has also been solved. Accordingly, the method of production of the present invention is industrially applicable as a method of producing a synthetic raw material for synthetic new quinolone antibacterial agents.

What is claimed is:

1. A method of producing 2-fluorocyclopropane-1-carboxylic acid ester, which comprises allowing a compound represented by the following formula (1):

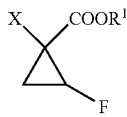

(1)

wherein X represents a chlorine atom, a bromine atom or an iodine atom; and $R^1$ represents an alkyl group having 1 to 8 carbon atoms, an aryl group having 6 to 12 carbon atoms, an alkenyl group having 2 to 8 carbon atoms, or an aralkyl group with an aryl group having 6 to 12 carbon atoms and an alkylene group having 1 to 6 carbon atoms; to react with a reducing agent in the presence of a phase transfer catalyst and a reaction solvent excluding dimethyl sulfoxide.

2. The method according to claim 1, wherein X in the formula (1) is a chlorine atom.

3. The method according to claim 1 wherein $R^1$ in the formula (1) is an alkyl group having 1 to 8 carbon atoms.

4. The method according to claim 3, wherein the alkyl group having 1 to 8 carbon atoms is a t-butyl group.

5. The method according to claim 1, wherein the phase transfer catalyst is a quaternary ammonium salt.

6. The method according to claim 5, wherein the quaternary ammonium salt is tetrabutylammonium bromide.

7. The method according to claim 5, wherein the quaternary ammonium salt is tetrabutylammonium chloride.

8. The method according to claim 5, wherein the quaternary ammonium salt is tetrabutylammonium hydrogen sulfate.

9. The method according to claim 5, wherein the quaternary ammonium salt is trioctylmethylammonium chloride.

10. The method according to claim 1, wherein the reducing agent is sodium borohydride.

11. The method according to claim 1, wherein the reducing agent represented by the following formula (3)

$$MBH_mR^2_n \qquad (3)$$

wherein M represents an alkali metal atom; $R^2$ represents a hydrogen atom, a cyano group, an alkoxy group or an acyloxy group, which alkoxy group or acyloxy group may be further substituted by a halogen atom; m is an integer of 1 to 4; n is an integer of 0 to 3; and the sum of m and n is 4.

12. The method according to claim 1, wherein the reaction solvent is water alone, a diluted hydrochloric acid or an aqueous sodium hydroxide solution, or a combination of water and at least one solvent selected from the group consisting of dialkyl ethers, toluene, benzene; ethyl acetate, tetrahydrofuran, acetonitrile, N,N-dimethylformamide, alcohol, hexane, heptane, octane and cyclohexane.

13. The method according to claim 12, wherein the reaction solvent is a combination of water and a solvent selected from the group consisting of diisopropyl ether, methyl t-butyl ether, cyclopentyl methyl ether, toluene, hexane, heptane, octane and cyclohexane.

14. The method according to claim 13, wherein the reaction solvent is a combination of water, methyl t-butyl ether and heptane.

15. The method according to claim 13, wherein the mixing ratio of water and the solvent is in the range of from 1:8 to 1:1.

16. The method according to claim 15, wherein the mixing ratio of water and the solvent is in the range of from 1:4 to 1:1.

17. The method according to claim 1, wherein the 2-fluorocyclopropane-1-carboxylic acid ester is produced as a mixture of cis and trans forms, in a ratio range of cis:trans of 87:13 to 97:3.

18. The method according to claim 17, wherein said compound of formula (1) is a mixture of cis and trans forms, and the content of trans form in said mixture of 2-fluorocyclopropane-1-carboxylic acid ester is less than the trans form content of said compound of formula (1), and the content of cis form in said mixture of 2-fluorocyclopropane-1-carboxylic acid ester is greater than the cis form content of said compound of formula (1).

19. The method according to claim 1, additionally comprising deriving 2-fluorocyclopropane-1-carboxylic acid from the 2-fluorocyclopropane-1-carboxylic acid ester.

20. The method according to claim 19, additionally comprising optically resolving the 2-fluorocyclopropane-1-carboxylic acid to produce 1,2-cis-2-fluorocyclopropane-1-carboxylic acid.